United States Patent [19]
Ecker et al.

[11] Patent Number: 5,523,389
[45] Date of Patent: Jun. 4, 1996

[54] INHIBITORS OF HUMAN IMMUNODEFICIENCY VIRUS

[75] Inventors: David J. Ecker, Leucadia; Jacqueline R. Wyatt, Carlsbad, both of Calif.; Jean L. Imbach, Montpellier, France

[73] Assignee: ISIS Pharmaceuticals, Inc., Carlsbad, Calif.

[21] Appl. No.: 128,011

[22] Filed: Sep. 28, 1993

Related U.S. Application Data

[63] Continuation-in-part of Ser. No. 954,185, Sep. 29, 1992, abandoned.

[51] Int. Cl.$^6$ .............................. C12N 15/11; C12Q 1/68
[52] U.S. Cl. ............................ 536/23.1; 435/6; 435/91.1; 435/172.1
[58] Field of Search .......................... 435/6, 91.1, 172.1; 536/23.1; 514/44

[56] References Cited

U.S. PATENT DOCUMENTS

| | | | |
|---|---|---|---|
| 5,034,506 | 7/1991 | Summerton et al. | 528/391 |
| 5,176,996 | 1/1993 | Hogan et al. | 435/6 |

FOREIGN PATENT DOCUMENTS

| | | |
|---|---|---|
| 9114436 | 3/1991 | WIPO . |
| 92/18518 | 10/1992 | WIPO . |
| 92/21690 | 12/1992 | WIPO . |
| 93/09788 | 5/1993 | WIPO . |

OTHER PUBLICATIONS

Sundquist et al. PNAS 90:3393–3397, Apr. 1993.
Stein et al. Science 261:1004 (1993).
Johnston et al. Science 260:1286 (1993).
Milligan et al. J. Med. Chem. 36:1923 (1993).
Aboul-ela et al., "NMR Study of Parallel-Stranded Tetraplex Formation by the Hexadeoxynucleotide d(TB$_4$T)" *Nature* 360: 280–282 (1992).
Agrawal, S. et al., "Oligodeoxynucleoside Phosphoramidates and Phosphorothioates as Inhibitors of Human Immunodeficiency Virus", *Proc. Nat'l. Acad. Sci. USA* 85: 7079–7083 (1988).
Agrawal, S. et al., "Inhibition of Human Immunodeficiency Virus in Early Infected and Chronically Infected Cells by Antisense Oligodeoxynucleotides and Their Phosphorothioate Analogues", *Proc. Natl. Acad. Sci. USA* 86: 7790–7794 (1989).
Bock et al., "Selection of Single-Stranded DNA Molecules that Bind and Inhibit Human Thrombin", *Nature* 355: 564–566 (1992).
Buck, H. M. et al., "Phosphate–Methylated DNA Aimed at HIV–1 RNA Loops and Integrated DNA Inhibits Viral Infectivity", *Science* 248: 208–212 (1990).
Callahan et al., "Dextran Sulfate Blocks Antibody Binding to the Principal Neutralizing Domain of Human Immunodeficiency Virus Type 1 without Interfering with gp120–CD4 Interactions", *J. Virol.* 65: 1543–1550 (1991).

Cheong and Moore, "Solution Structure of an Unusually Stable RNA Tetraplex Containing G– and U–Quartet Structures", *Biochemistry* 31: 8406–8414 (1992).
Ecker et al., "Rational Screening of Oligonucleotide Combinatorial Libraries for Drug Discovery", *Nucleic Acids Res.* l 21: 1853–1856 (1993).
Foley et al., "Continuous Culture of Human Lymphoblasts From Peripheral Blood of a Child with Acute Leukemia" *Cancer* 18: 522–529 (1965).
Fouchier et al., "Phenotype–Associated Sequence Variation in the Third Variable Domain of the Human Immunodeficiency Virus Type 1 gp120 Molecule", *J. Virol* 66:, 3183–3187 (1992).
Fried and Crothers, "Equilibria and Kinetics of Lac Repressor–Operator Interactions by Polyacrylamide Gel Electrophoresis", *Nucleic Acids Res* 9: 6505–6525 (1981).
Gama Sosa et al., "Human Cell Lines Stably Expressing HIV env and tat Gene Products", *Biochem. Biophys. Res. Comm.* 161: 305–311 (1989).
Geysen et al., "A Priori Delineation of a Peptide Which Mimics a Discontinuous Antigenic Determinant", *Mol. Immunol.* 23: 709–715 (1986).
Goodchild et al., "Inhibition of Human Immunodeficiency Virus Replication by Antisense Oligodeoxynucleotides", Proc. Natl. Acad. Sci. USA 85: 5507–5511 (1988).
Guschlbauer et al., "Four–Stranded Nucleic Acid Structures 25 Years Later From Guanosine Gels to Telomer DNA", *J. Biomol. Str. Dyn.* 8: 491–511 (1990).
Hardin et al., "Cation–Dependent Transition Between the Quadruplex and Watson–Crick Hairpin Forms of d(CGCG$_3$GCG)", *Biochemistry* 31: 833–841 (1992).
Healey et al., "Novel Anti–CD4 Monoclonal Antibodies Separate Human Immunodeficiency Virus Infection and Fusion of CD4$^+$ Cells from Virus Binding", *J. Exp. Med.* 172: 1233–1242 (1990).
Houghten et al., "Generation and Use of Synthetic Peptide Combinatorial Libraries for Basic Research and Drug Discovery", *Nature* 354: 84–86 (1991).
Iyer et al., "The Automated Synthesis of Sulfur–Containing Oligodeoxyribonucleotides Using 3H–1, 2–Benzodithiol–3–one 1, 1–Dioxide as a Sulfur–Transfer Reagent", *J. Org. Chem.* 55: 4693–4699 (1990).

(List continued on next page.)

*Primary Examiner*—John L. LeGuyader
*Attorney, Agent, or Firm*—Woodcock Washburn Kurtz Mackiewicz & Norris

[57] ABSTRACT

The phosphorothioate oligonucleotide T$_2$G4T$_2$ was identified as an inhibitor of HIV infection in vitro by combinatorial screening of a library of phosphorothioate oligonucleotides that contained all possible 8-nucleotide sequences. The oligonucleotide forms a parallel-stranded tetrameric guanosinequartet (G-quartet) structure. Tetramer formation and the phosphorothioate backbone are essential for antiviral activity. The G-quartet structure binds to the HIV envelope protein gp120 at the V3 loop and inhibits both cell-to-cell and virus-to-cell infection.

1 Claim, 4 Drawing Sheets

OTHER PUBLICATIONS

Jin et al., "Thermodynamics and Structure of a DNA Tetraplex: A Spectroscopic and Calorimetric Study of the Tetramolecular Complexes of d(TG$_3$T) and d(TG$_3$T$_2$G$_3$T)", *Proc. Natl. Acad. Sci. USA* 89: 8832–8836 (1992).

Kim et al., "Tetramerization of an RNA Oligonucleotide Containing a GGGG Sequence", *Nature* 351: 331–332 (1991).

Kimpton and Emerman, "Detection of Replication–Competent and Pseudotyped Human Immunodeficiency Virus with a Sensitive Cell Line on the Basis of Activation of an Integrated β–Galactosidase Gene", *J. Virol* 66: 2232–2239 (1992).

Letsinger et al., "Cholesteryl–Conjugated Oligonucleotides: Synthesis, Properties, and Activity as Inhibitors of Replication of Human Immunodeficiency Virus in Cell Culture", *Proc. Natl. Acad. Sci. USA* 86: 6553–6556 (1989).

Lu et al, "Structure and Stability of Sodium and Potassium Complexes of dT$_4$G$_4$ and dT$_4$G$_4$T", *Biochemistry* 31: 2455–2459 (1992).

Matsukura et al., "Phosphorothioate Analogs of Oligodeoxynucleotides: Inhibitors of Replication and Cytophatic Effects of Human Immunodeficiency Virus", *Proc. Natl. Acad. Sci. USA* 84: 7706–7710 (1987).

Matsushita et al., "Characterization of a Human Immunodeficiency Virus Neutralizing Monoclonal Antibody and Mapping of the Neutralizing Epitope", *J. Virol.* 62: 2107–2114 (1988).

Putney et al., "HTLV–III/LAV–Neutralizing Antibodies to an E. coli–Produced Fragment of the Virus Envelope", *Science* 234: 1392–1395 (1986).

Mori et al., "Phosphoroselenoate Oligodeoxynucleotides: Synthesis, Physico–Chemical Characterization, Anti–Sense Inhibitory Properties and Anti–HIV Activity", *Nucleic Acids Res.* 17: 8207–8219 (1989).

Morvan et al., "α–DNA II. Synthesis of Unnatural α–anomeric Oligodeoxyribonucleotides Containing the Four Usual Bases and Study of Their Substrate Activities for Nucleases", *Nucleic Acids Res.* 15: 3421–3437 (1993).

Nara and Fischinger, "Quantitative Infectivity Assay for HIV–1 and –2" *Nature* 332: 469–470 (1988).

Nielsen et al., "Sequence–Selective Recognition of DNA by Strand Displacement with a Thymine–Substituted Polyamide", *Science* 254: 1497–1500 (1991).

Owens et al., "The Rapid Identification of HIV Protease Inhibitors Through the Synthesis and Screening of Defined Peptide Mixtures", *Biochem. Biophys. Res. Commun.* 181: 402–408 (1991).

Puglisi & Tinoco, "Absorbance Melting Curves of RNA", In *Methods in Enzymology, RNA Processing,* eds. Dahlberg, J. E. & Abelson, J. N. (Academic Press, Inc., New York), vol. 180, 304–324 (1989).

Ruprecht et al., "Castanospermine vs. Its 6–0–Butanoyl Analog: A Comparison of Toxicity and Antiviral Activity In Vitro and In Vivo", *J. Acquir. Immune Defic. Syndr.* 4: 48–55 (1991).

Rusche et al., "Humoral Immune Response to the Entire Human Immunodeficiency Virus Envelope Glycoprotein Made in Insect Cells", *Proc. Natl. Acad. Sci. USA* 84: 6924–6928 (1987).

Sarin et al., "Inhibition of Acquired Immunodeficiency Syndrome Virus by Oligodeoxynucleoside Methylphosphonates", *Proc. Natl. Acad. Sci. USA* 85: 7448–7451 (1988).

Sarma et al., "Tetraplex Formation of d(GGGGGTTTTT): $^1$H NMR Study in Solution", *J. Biomol. Str. Dyn* 9: 1131–1153 (1992).

Sen and Gilbert, "Novel DNA Superstructures Formed by Telomere–Like Oligomers", *Biochemistry* 31: 65–70 (1992).

Sen and Gilbert, "A Sodium–Potassium Switch in the Formation of Four–Stranded G4–DNA" *Nature* 344: 410–414 (1990).

Shibahara et al., "Inhibition of Human Immunodeficiency Virus (HIV–1) Replication by Synthetic Oligo–RNA Derivatives", *Nucl. Acids Res.* 17: 239–252 (1989).

Srivastava et al., "Human Immunodeficiency Virus Type 1 NL4–3 Replication in Four T–Cell Lines: Rate and Efficiency of Entry, a Major Determinant of Permisiveness", *J. Virol* 65: 3900–3902 (1991).

Stein et al., "Phosphorothioate Oligodeoxycytidine Interferes with Binding of HIV–1 gp120 to CD4", J. Acquir. Immune Defic. Syndr. 4: 686–693 (1991).

Stevenson and Iversen, "Inhibition of Human Immunodeficiency Virus Type 1–Mediated Cytophatic Effects by Poly(L–lysine)–Conjugated Synthetic Antisense Oligodeoxyribonucleotides", *J. Gen. Virol.* 70: 2673–2682 (1989).

Tuerk et al., "RNA Pseudoknots that Inhibit Human Immunodeficiency Virus Type 1 Reverse Transcriptase", *Proc. Natl. Acad. SCi. USA* 89: 6988–6992 (1992).

Tuerk and Gold, "Systematic Evolution of Ligands by Exponential Enrichment: RNA Ligands to Bacteriophage T4 DNA Polymerase", *Science* 249: 505–510 (1990).

Vickers et al., "Inhibition of HIV–LTR Gene Expression by Oligonucleotides Targeted to the TAR Element", *Nucleic Acids Res.* 19: 3359–3368 (1991).

Wang and Patel, "Guanine Residues in d(T$_2$AG$_3$) and d(T$_2$G$_4$) Form Parallel–Stranded Potassium Ction Stabilized G–Quadruplexes with Anti Glycosidic Torsion Angles in Solution", *Biochemistry* 31: 8112–8119 (1992).

White et al., "A TIBO Derivative, R82913, is a Potent Inhibitor of HIV–1 Reverse Transcriptase With Heteropolymer Templates", *Antiviral Res.* 16: 257–266 (1991).

Williamson, "Guanine Quartets", *Curr. Opin. Struct. Biol.* 3, 357–362 (1993).

Zaia et al., "Inhibition of Human Immunodeficiency Virus by Using an Oligonucleoside Methylphosphonate Targeted to the TAT–3 Gene", *J. Virol.* 62: 3914–3917 (1988).

Zamecnik et al., "Inhibition of Replication and Expression of Human T–Cell Lymphotropic Virus Type III in Cultured Cells by Exogenous Synthetic Oligonucleotides Complementary to Viral RNA", *Proc. Natl. Acad. Sci. USA* 83: 4143–4146 (1986).

McShan et al., "Inhibition of Transcription of HIV–1 in Infected Human Cells by Oligodeoxynucleotides Designed to Form DNA Triple Helices", *J. Biol. Chem.* 267: 5712–5721 (1992).

Shida et al., "Self–Association of Telomeric Short Oligodeoxynucleotides Containing a dG Cluster", *Chem. Pharm. Bull.* 39: 2207–2211 (1991).

Malvy et al., "Specific Inhibition of Retroviruses and Retrovirus Activated Oncoproteins by Antisense Oligonucleotides", *Antiviral Research 20 Supp I:* 80 (1993).

Guschlbauer and Jankowski, "Nucleoside Conformation is Determined by the Electronegativity of the Sugar Substituent", *Nucleic Acids Research* 8: 1421–1433 (1980).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

GGGGTTTTGG GG            12

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

GGGTTTTGGG            10

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

GGGGGTTTTT            10

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:4:

TTTTTTTTTT TTTGGGGTTT T            21

INHIBITORS OF HUMAN IMMUNODEFICIENCY VIRUS

CROSS REFERENCE TO RELATED APPLICATION

This application is a continuation-in-part of copending application U.S. Ser. No. 07/954,185 filed Sep. 29, 1992 now abandoned.

FIELD OF THE INVENTION

This invention relates to oligonucleotides useful for the treatment of viruses such as human immunodeficiency virus and methods of use thereof.

BACKGROUND OF THE INVENTION

There have been many approaches for inhibiting the activity of viruses such as the human immunodeficiency virus (HIV), herpes simplex virus (HSV), human cytomegalovirus (HCMV) and influenza. Such prior art methods include nucleoside analogs (e.g., HSV) and antisense oligonucleotide therapies (e.g., HIV, influenza).

Prior attempts to inhibit HIV by various approaches have been made by a number of researchers. For example, Zamecnik and coworkers have used phosphodiester antisense oligonucleotides targeted to the reverse transcriptase primer site and to splice donor/acceptor sites, P. C. Zamecnik, J. Goodchild, Y. Taguchi, P.S. Sarin, *Proc. Natl. Acad. Sci. USA* 1986, 83, 4143. Goodchild and coworkers have made phosphodiester antisense compounds targeted to the initiation sites for translation, the cap site, the polyadenylation signal, the 5' repeat region and a site between the gag and pol genes. J. Goodchild, S. Agrawal, M. P. Civeira, P. S. Sarin, D. Sun, P. C. Zamecnik, *Proc. Natl. Acad. Sci. U.S.A.* 1988, 85, 5507. Agrawal and coworkers have used chemically modified antisense oligonucleotide analogs targeted to the cap and splice donor/acceptor sites. S. Agrawal, J. Goodchild, M. P. Civeira, A. H. Thornton, P. S. Sarin, P. C. Zamecnik, *Proc. Nat'l Acad. Sci. USA* 1988, 85, 7079. Agrawal and coworkers have used antisense oligonucleotide analogs targeted to the splice donor/acceptor site inhibit HIV infection in early infected and chronically infected cells. S. Agrawal, T. Ikeuchi, D. Sun, P. S. Sarin, A. Konopka, J. Maizel, *Proc. Natl. Acad. Sci. U.S. A.* 1989, 86, 7790.

Sarin and coworkers have also used chemically modified antisense oligonucleotide analogs targeted to the HIV cap and splice donor/acceptor sites. P. S. Sarin, S. Agrawal, M. P. Civeira, J. Goodchild, T. Ikeuchi, P. C. Zamecnik, *Proc. Natl. Acad. Sci. U. S. A.* 1988, 85, 7448. Zaia and coworkers have also used an antisense oligonucleotide analog targeted to a splice acceptor site to inhibit HIV. J. A. Zaia, J. J. Rossi, G. J. Murakawa, P. A. Spallone, D. A. Stephens, B. E. Kaplan, *J. Virol.* 1988, 62, 3914. Matsukura and coworkers have synthesized antisense oligonucleotide analogs targeted to the initiation of translation of the HIV rev gene mRNA. M. Matsukura, K. Shinozuka, G. Zon, *Proc. Natl. Acad. Sci. USA* 1987, 84, 7706; R. L. Letsinger, G. R. Zhang, D. K. Sun, T. Ikeuchi, P. S. Sarin, *Proc. Natl. Acad. Sci. U.S.A.* 1989, 86, 6553. Mori and coworkers have used a different antisense oligonucleotide analog targeted to the same region as Matsukura. K. Mori, C. Boiziau, C. Cazenave, *Nucleic Acids Res.* 1989, 17, 8207. Shibahara and coworkers have used antisense oligonucleotide analogs targeted to a splice acceptor site as well as the reverse transcriptase primer binding site. S. Shibahara, S. Mukai, H. Morisawa, H. Nakashima, S. Kobayashi, N. Yamamoto, *Nucl. Acids Res.* 1989, 17, 239. Letsinger and coworkers have synthesized and tested a oligonucleotide analogs with conjugated cholesterol targeted to a splice site. K. Mori, C. Boiziau, C. Cazenave, *Nucleic Acids Res.* 1989, 17, 8207. Stevenson and Iversen have conjugated polylysine to antisense oligonucleotide analogs targeted to the splice donor and the 5'-end of the first exon of the HIV tat gene. M. Stevenson, P. L. Iversen, *J. Gen. Virol.* 1989, 70, 2673. Buck and coworkers have described the use of phosphatemethylated DNA oligonucleotides targeted to HIV mRNA and DNA. H. M. Buck, L. H. Koole, M. H. P. van Gendersen, L. Smith, J. L. M. C. Green, S. Jurriaans and J. Goudsmit, *Science* 1990, 248, 208–212. These prior attempts at inhibiting HIV activity have largely focused on the nature of the chemical modification used in the oligonucleotide analog.

Guanosine nucleotides, both as mononucleotides and in oligonucleotides or polynucleotides, are able to form arrays known as guanine quartets or G-quartets. For review, see Williamson, J. R., (1993) *Curr. Opin. Struct. Biol.* 3:357–362. G-quartets have been known for years, although interest has increased in the past several years because of their possible role in telomere structure and function. One analytical approach to this area is the study of structures formed by short oligonucleotides containing clusters of guanosines, such as GGGGTTTTGGGG (SEQ ID NO: 1), GGGTTTTGGG (SEQ ID NO: 2), UGGGGU, GGGGGTTTTT (SEQ ID NO: 3), TTAGGG, TTGGGG and others reviewed by Williamson; TTGGGGGTT described by Shida et al. (Shida, T., Yokoyama, K., Tamai, S., and J. Sekiguchi (1991) *Chem. pharm. Bull.* 39:2207–2211), among others.

It has now been discovered that in addition to their natural role (in telomeres, for example, though there may be others), oligonucleotides which form G-quartets and oligonucleotides containing clusters of G's are useful as drugs for inhibiting viral gene expression or viral growth and for inhibiting $PLA_2$ enzyme activity, and may be useful as modulators of telomere length. Chemical modification of the oligonucleotides for use as drugs is desirable and, in some cases, necessary.

Guanosine-rich oligonucleotides have been observed in superstructures formed by G-rich oligonucleotides with terminal guanosines. Lu, M., Guo, Q. & Kallenbach, N. R. (1992) *Biochemistry* 31, 2455–2459; Sen, D. & Gilbert, W. (1992) *Biochemistry* 31, 65–70. The role of the multimeric structures in antiviral activity is not known and the structures were not characterized further.

Oligonucleotides containing only G and T have been designed to form triple strands with purine-rich promotor elements to inhibit transcription. These triplex-forming oligonucleotides (TFOs), 28 to 54 nucleotides in length, have been used to inhibit expression of the oncogene c-erb B2/neu (WO 93/09788, Hogan). Amine-modified TFOs 31-38 nucleotides long have also been used to inhibit transcription of HIV. McShan, W. M. et al. (1992) *J. Biol. Chem.* 267:5712–5721. Although each of the above publications have reported some degree of success in inhibiting some function of the virus, a general therapeutic scheme to target HIV and other viruses has not been found.

Accordingly, there has been and continues to be a long-felt need for the design of compositions which are capable of effective, therapeutic use. The present invention is directed to meeting these and other important needs.

SUMMARY OF THE INVENTION

In accordance with some embodiments of the present invention is provided compounds comprising a G-quartet structure of phosphorothioate oligonucleotides each oligonucleotide comprising the sequence TxG4Ty where x and y are independently 0 to 8.

Methods for inhibiting the activity of human immunodeficiency virus are also provided comprising administering to a cell infected with said virus a compound comprising a G-quartet structure of phosphorothioate oligonucleotides each oligonucleotide having the sequence TxG4Ty where x and y are independently 0 to 8 in an amount sufficient to inhibit the activity of the virus.

In other embodiments of the present invention methods for treating a patient infected with human immunodeficiency virus are provided comprising administering to said patient a compound comprising a G-quartet structure of phosphorothioate oligonucleotides having the sequence TxG4Ty where x and y are independently 0 to 8 in an amount sufficient to inhibit the activity of the virus.

Pharmaceutical compositions are also provided comprising compounds comprising a G-quartet structure of phosphorothioate oligonucleotides having the sequence TxG4Ty where x and y are independently 0 to 8 and in a pharmaceutically acceptable carrier.

These and other features of the invention will become apparent to persons of ordinary skill in the art from a review of the instant specification and appended claims.

DETAILED DESCRIPTION OF PREFERRED EMBODIMENTS

Specific binding of nucleic acids to proteins regulates cellular functions at many levels. Considerable attention has recently been directed to the use of synthetic nucleic acids as ligands to modulate the activities of proteins for therapeutic purposes. Several in vitro strategies have been developed to selectively screen for nucleic acid sequences that bind to specific proteins; Tuerk, C. & Gold, L. (1990) *Science* 249, 505–510; Tuerk, C., et al., (1992) *Proc. Natl. Acad. Sci. USA* 89, 6988–6992; including proteins that are not naturally bound by nucleic acids. Bock, L. C., et al., (1992) *Nature* 355, 564–566.

The selection strategy known as synthetic unrandomization of randomized fragments (SURF); Ecker, D. J., Vickers, T. A., Hanecak, R., Driver, V. & Anderson, K. (1993) *Nucleic Acids Res.* 21, 1853–1856; is employed to screen libraries of oligonucleotides for activity such as anti-viral activity. This type of selection technique; Geysen, H. M., et al. (1986) *Mol. Immunol.* 23, 709–715; Houghten, R. A., et al., (1991) *Nature* 354, 84–86; and Owens, R. A., et al., (1991) *Biochem. Biophys. Res. Commun.* 181,402–408; involves iterative synthesis and screening of increasingly simplified sets of oligonucleotide pools. Oligonucleotide analogs can be used in the libraries because this technique does not require enzymes either to synthesize the randomized pools or to amplify the active molecular species. The use of nuclease-resistant oligonucleotide analogs allows screening for functional activities in cell culture systems in which unmodified RNA or DNA is rapidly degraded. Assay of compound libraries in the presence of whole viruses and cells provides the opportunity to screen "a library of compounds" against "a library of targets," potentially inhibiting any step in the viral life cycle. Since functional inhibition of viral infection rather than nucleic acid binding is the selection criterion, the chances are enhanced that a useful compound will be identified.

When the SURF strategy was used in a functional screen for an inhibitor of vital infection, phosphorothioate oligonucleotides with four consecutive guanosines (Gs) were found to have activity. No strong selection preference was observed for nucleotides flanking the guanosine "core" thus nucleotides flanking the guanosine core may be any nucleotide selected from naturally occurring and synthetic bases. For example, flanking oligonucleotides may be selected from A, T, G and C. Oligonucleotide comprising the sequence $T_xG_4T_y$ are preferred in some embodiments of the present invention wherein x and y are independently 0 to about 8. In some preferred embodiments of the present invention x is 2 and y is 2. In still other embodiments of the present invention x is 0 and y is 2. In yet other embodiments of the present invention x is 3 and y is 3.

In other embodiments of the present invention oligonucleotides comprising the sequence $(T_xG_4T_y)_q$ are preferred wherein x and y are independently 0 to about 8 as described above, and q is from 1 to about 10. In some embodiments of the present invention it may be preferred that q is from 1 to about 3. In other embodiments of the present invention it is preferred that q is from about 2 to about 5. q may be from about 4 to about 7 in yet other preferred embodiments and may range from about 6 to about 10 in still other embodiments.

Physical characterization of oligonucleotides comprising at least four consecutive guanosines demonstrated that such oligonucleotides form a tetramer stabilized by G-quartets. G-quartet structures are intra- or inter-molecular four-stranded helices stabilized by planar Hoogsteen-paired quartets of guanosine. Guschlbauer, W., et al., (1990) *J. Biomol. Str. Dyn.* 8,491–511 and Williamson, J. R. (1993) *Curr. Opin. Struct. Biol.* 3,357–362. The structures are stabilized by monovalent ions bound between two planes of G-quartets and coordinated to the carbonyl oxygens. Cell culture experiments of the G-quartet made up of oligonucleotides having the sequence $T_2G_4T_2$ revealed that the G-quartet structure blocks both HIV virion binding to cells and virus-mediated cell fusion.

Virus and cell membrane fusion is initiated by binding of gp120, the major envelope protein of HIV, to its cellular receptor. The mechanism by which membrane fusion occurs is not well understood, but a particular region of gp120, the V3 loop, is essential. (1992) *Human Retroviruses and AIDS* 1992, eds. Myers, G. et al. (Theoretical Biology and Biophysics, Los Alamos National Laboratory, Los Alamos, N. Mex.). The V3 loop maintains a high percentage of positively charged amino acids across all HIV strains; Callahan, L., et al., (1991) *J. Virol.* 65, 1543–1550; and the extent of virus-mediated cell fusion and rapid viral replication have been correlated with increased cationic composition of the V3 loop. Fouchier, R. A. M., et al., (1992) *J. Virol.* 66, 3183–3187. In vitro studies showed that the G-quartet structure bound directly to the V3 loop of gp120. Thus the G-quartet structure provides a novel scaffold to present the backbone groups such as phosphorothioate groups in a favorable orientation for binding to the highly cationic V3 loop.

In the context of the present invention, the following abbreviations for the commonly occurring nucleic acid bases are used. "A" refers to adenosine, "T" refers to thymidine, "G" refers to guanosine, "C" refers to cytidine and "U" refers to uridine.

The strands of oligonucleotides which form oligonucleotide compounds of the present invention preferably comprise from about 4 to about 50 nucleic acid base units. It is more preferred that such oligonucleotides comprise from 6 to 32 nucleic acid base units, and still more preferred to have from about 6 to 24 nucleic acid base units.

In some preferred embodiments of the present invention, at least one oligonucleotide of G-quartets of the present invention has an alpha ($\alpha$) anomeric configuration. In the context of the present invention an alpha anomeric configuration is one in which the N-glycosidic bond is inverted.

In preferred embodiments of the present invention, oligonucleotides have phosphorothioate intersugar linkages (or backbone) since a parallel complex will orient phosphorothioate groups in a favorable orientation. In some embodiments of the present invention at least about 50% of the inter-sugar linkages are phosphorothioate linkages. In still other embodiments of the from about at least about 75% of the intersugar linkages are phosphorothioate linkages. In still further embodiments of the present invention approximately 100% of the inter-sugar linkages are phosphorothioate linkages.

In addition, it will be appreciated by those skilled in the art that other backbone modifications may be employed in some aspects of the present invention.

Some preferred oligonucleotides useful in some aspects of the present invention may include intersugar linkages such as phosphotriesters, methyl phosphonates, chain alkyl or cycloalkyl intersugar linkages or short chain heteroatomic or heterocyclic intersugar linkages including those with $CH_2$—NH—O— $CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—P—O—$CH_2$). Oligonucleotides having morpholino backbone structures may also be useful in some aspects of the invention. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497.

Other preferred oligonucleotides may contain alkyl and halogen-substituted sugar moieties comprising one of the following at the 2' position: OH, SH, $SCH_3$, F, $OCN$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In accordance with methods of the present invention, oligonucleotide compounds of the present invention may be administered to cells infected with a virus such as human immunodeficiency virus to inhibit viral activity. In some aspects of the invention, a significant level of inhibitory activity means at least 50% inhibition of activity as measured in an appropriate, standard assay. Such assays are well known to those skilled in the art. More or less inhibition may be suitable for other embodiments of the present invention.

Oligonucleotide compounds of the present invention may be administered to patients infected with human immunodeficiency virus. One skilled in the art will appreciate that the optimal dose and methodology will vary depending upon the age, size and condition of a patient. Administration is generally continued until symptoms associated with infection of said virus are diminished or eliminated.

Oligonucleotide compounds of the present invention may be incorporated in a pharmaceutically acceptable carrier and may be incorporated in compositions suitable for a variety of modes of administration. In one embodiment of the present invention, oligonucleotide compounds of the present invention are coated on a prophylactic device such as latex gloves or condoms. In still another embodiment of the present invention oligonucleotide compounds are prepared for topical application such as in a cream or salve. Of course oligonucleotide compounds of the present invention may be prepared to suit any number of modes of administration as necessary for a given condition.

The following examples are illustrative of the invention and are not intended to limit the invention in any way.

EXAMPLES

Example 1

Oligonucleotide synthesis.

Phosphorothioate oligonucleotides were synthesized using standard protocols. Sulfurization was achieved using 3H-1,2-benzodithiole-3-one-1,1 dioxide ("Beaucage reagent") as oxidizing agent. Iyer, R. P., Phillips, L. R., Egan, W., Regan, J. B. & Beaucage, S. L. (1990) *J. Org. Chem.* 55, 4693–4699. For oligonucleotides with randomized positions, amidites were mixed in a single vial on the fifth port of the ABI 394 synthesizer. The mixture was tested by coupling to dT-CPG, cleaving and deprotecting the product, and analyzing the crude material on reversed-phase HPLC. Proportions of the individual amidites were adjusted until equal amounts of the four dimers were obtained. DMT-off oligonucleotides were purified by reversed-phase HPLC with a gradient of methanol in water to desalt and remove the protecting groups. Several purified oligonucleotides were analyzed for base composition by total digestion with nuclease followed by reversed-phase HPLC analysis and yielded expected ratios of each base.

Oligonucleotides with the α-configuration of the glycosidic bond were synthesized as previously described. Motvan, F., Raynet, B., Imbach, J-L., Thenet, S., Bertrand, J-R., Paoletti, J., Malvy, C. & Paoletti, C. (1993) *Nucleic Acids Res.* 15, 3421–3437. Biotin was incorporated during chemical synthesis using biotin-linked CPG from Glen Research to form biotinylated oligonucleotide. Oligonucleotide $T_2G_4T_2$ was purified by reverse phase chromatography to remove salts and protecting groups and then by size exclusion chromatography to purify the tetramer as described in Example 3.

Prior to antiviral screening, oligonucleotides were diluted to 1 mM strand concentration in 40 mM sodium phosphate (pH 7.2), 100 mM KCl and incubated at room temperature overnight. Extinction coefficients were determined as described by Puglisi & Tinoco, (1989) In *Methods in Enzymology, RNA Processing*, eds. Dahlberg, J. E. & Abelson, J. N. (Academic Press, Inc., New York), Vol. 180, pp. 304–324. Samples were filtered through 0.2 μm cellulose acetate filters to sterilize.

Example 2

Antiviral assay.

Oligonucleotides were screened in an acute HIV-1 infection assay which measures protection from HIV-induced cytopathic effects. The CEM-SS cell line; Nara, P. L. & Fischinger, P. J. (1988) *Nature* 332,469–470; was maintained in RPMI 1640 medium supplemented with 10% fetal bovine serum, 2 mM glutamine, penicillin (100 units $mL^{-1}$), and streptomycin (100 μg $mL^{-1}$). The antiviral assay, using XTT-tetrazolium to quantitate drug-induced protection from HIV-induced cell killing has been described. White, E. L., Buckheit, Jr., R. W., Ross, L. J., Germany, J. M., Andries, K., Pauwels, R., Janssen, P. A. J., Shannon, W. M. & Chirigos, M. A. (1991) Antiviral Res. 16, 257–266.

Example 3

Characterization of tetramer.

A 1 mM stock of ISIS 5320 in 40 mM sodium phosphate (pH 7.2), 100 mM KCl was diluted to 10 μM into PBS (137 mM NaCl; 2.7 mM KCl; 1.5 mM potassium phosphate monobasic; 8 mM sodium phosphate dibasic) and incubated at 37° C. Aliquots were analyzed for dissociation following dilution by determining percent monomeric and tetrameric forms of oligonucleotides by separation on a Pharmacia Superdex HR 10/30 size exclusion column (Pharmacia, Upsalla, Sweden). Running buffer was 25 mM sodium phosphate (pH 7.2), 0.2 mM EDTA. Flow rate was 0.5 mL $min^{-1}$ and detection was at 260 nm.

Figure 1A:
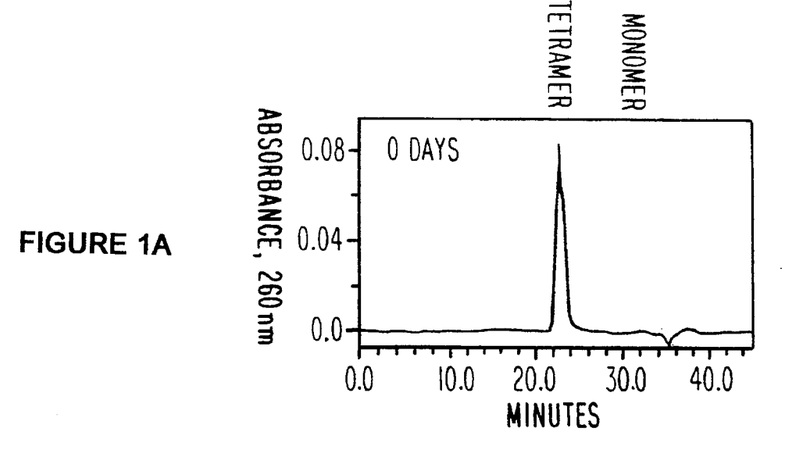
FIGS. 1A–1C are line plots showing dissociation of ISIS 5320 tetramer monitored by size exclusion chromatography over a period of 1 to 131 days.
Figure 1B:
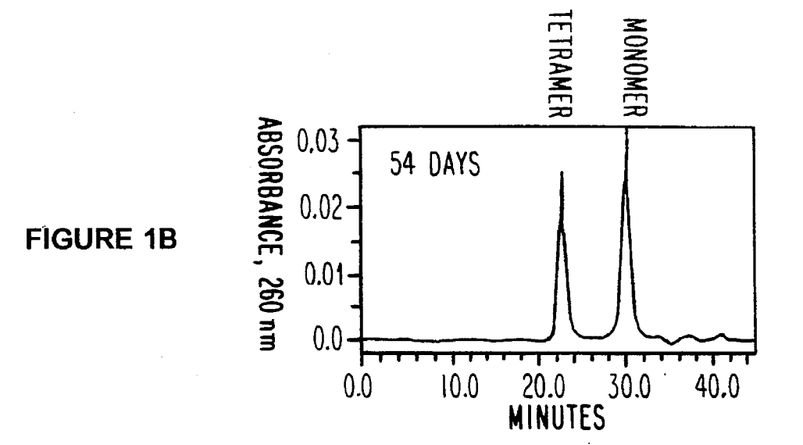
Figure 1C:
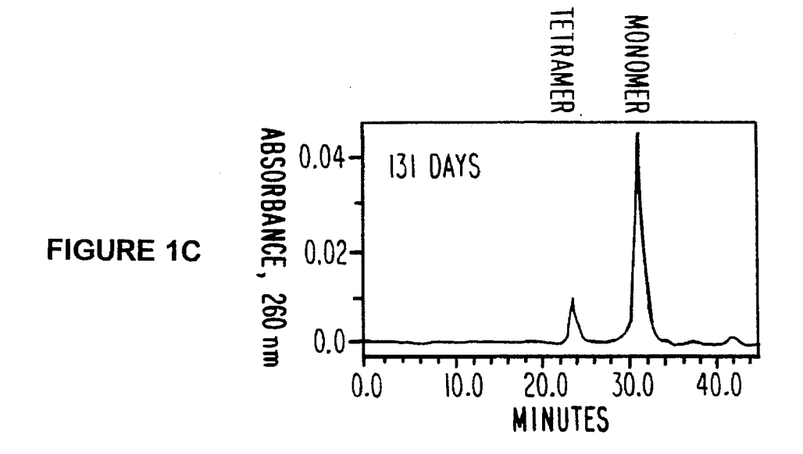

Monomer and tetramer peaks were integrated and fraction tetramer determined. The tetramer eluted at 22.8 min and the monomer at 30.5 minutes. FIG. 1 shows the dissociation of tetramer ISIS 5320 for 0, 54 and 131 days.

For purification, a Pharmacia Superdex 75 HiLoad 26/60 column was used with a buffer of 10 mM sodium phosphate (pH 7.2) at a flow rate of 2 mL $min^{-1}$.

Figure 3:
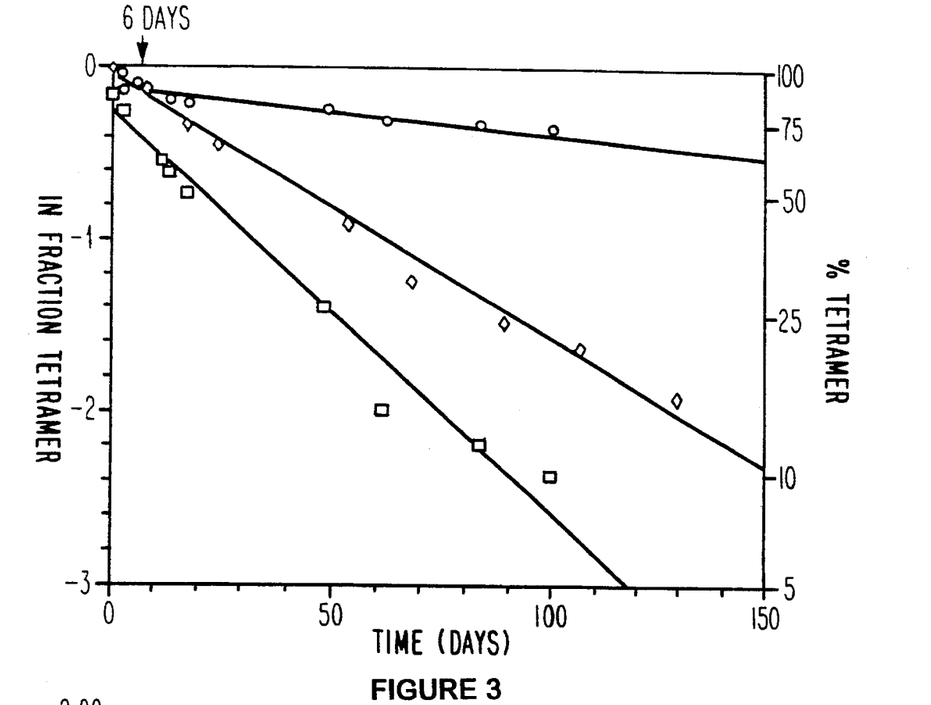
FIG. 3 is a line graph showing dissociation of tetramers formed by phosphorothioate ISIS 5320 in Na+ (squares), ISIS 5320 in K+ (diamonds) and the phosphodiester version (circles) over a period of days.

1 mM solution of oligonucleotide was diluted to 10 μM into PBS (137 mM NaCl; 2.7 mM KCl; 1.5 mM potassium phosphate monobasic; 8 mM sodium phosphate dibasic) and incubated at 37° C. This level is a level used in antiviral assays. Specifically ISIS 5320 in $K^+$ and the phosphodiester $T_2G_4T_2$ were diluted from solutions in 40 mM sodium phosphate (pH 7.2), 100 mM KCl. ISIS 5320 in $Na^+$ was diluted from a solution in 40 mM sodium phosphate (pH 7.2), 100 mM NaCl. Dissociation as a function of time was followed by size exclusion chromatography as described above. Results shown in FIG. 3 show the dissociation of oligonucleotides in $Na^+$ and $K^+$. The potassium form preferentially stabilized the tetramer with a half life for the dissociation of the potassium form of ISIS 5320 is about 45 days. However, the dissociation of the tetramer in either form was relatively slow and both sodium and potassium forms have the same $IC_{50}$ values in the acute antiviral assay.

Figure 2:
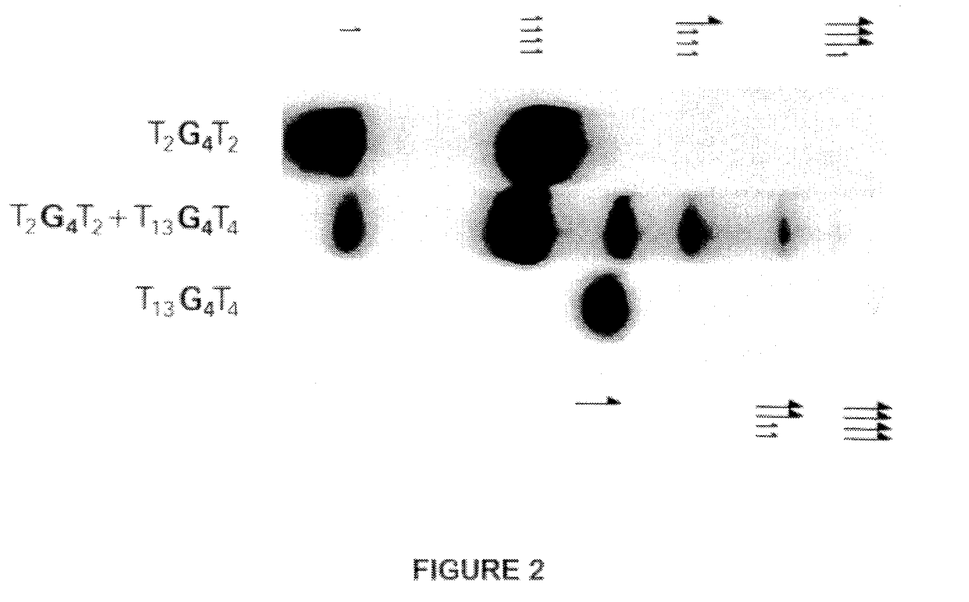
FIG. 2 is an autoradiogram of a gel electrophoresis experiment showing a pattern characteristic of a parallel-stranded tetramer. Lane 1: ISIS 5320 ($T_2G_4T_2$) alone. Lane 2: ISIS 5320 incubated with $T_{13}G_4G_4$ (SEQ ID NO: 4). Lane 3: $T_{13}G_4T_4$ (SEQ ID NO: 4 ) alone.

The tetramer formed was parallel-stranded as determined by analysis of the complexes formed by the phosphorothioate oligonucleotides having $T_2G_4T_2$ and $^{5'}T_{13}G_4T_4^{3'}$ (SEQ ID NO: 4). Each oligonucleotide was labeled at the 5' end with $^{32}P$. Each sample contained 125 μM unlabeled and 15 pM radioactively labeled amounts of one or both of the oligonucleotides. The samples were heated in 50 mM sodium phosphate (pH 7.2), 200 mM KCl in a boiling water bath for 15 min then incubated for 48 h at 4° C. Samples were analyzed by autoradiography of a 20% non-denaturing polyacrylamide (19:1, acrylamide: bis) gel run at 4° C. in 1× TBE running buffer. FIG. 2. Lane 1: ISIS 5320 ($T_2G_4T_2$) alone. Lane 2: ISIS 5320 incubated with $T_{13}G_4G_4$ (SEQ ID NO: 4). Lane 3: $T_{13}G_4T_4$ (SEQ ID NO: 4) alone. The pattern, five aggregate species, is characteristic of parallel-stranded tetramer.

Example 4

Assay of virus-induced cell fusion.

Stoichiometric amounts of chronically HIV-1-infected Hut 78 cells (Hut/4-3) and CD4+ HeLa cells harboring an LTR-driven lac z gene were co-cultured for 20 h in the presence or absence of oligonucleotide. Cells were fixed (1% formaldehyde, 0.2% glutaraldehyde in PBS) and incubated with X-gal until cell-associated color developed. After buffer removal, a standard o-nitrophenyl-β-D-galactopyranoside was used to quantitate β-galactosidase expression. As a control, HeLa CD4+ cells containing the LTR-driven lac z gene were transfected using the calcium phosphate method with 30 μg of proviral DNA (pNL 4-3). Oligonucleotide was added immediately after the glycerol shock. Cells were fixed 48 h after transfection and assayed as described above.

Example 5

Binding of ISIS 5320 to gp120.

Direct binding to gp120 was assayed using immobilized gp120 from a CD4 capture ELISA kit (American Biotechnologies). Biotinylated oligonucleotides were incubated in a volume of 100 μL with immobilized gp120. Following a 1 hour incubation wells were washed and 200 μL of streptavidin-alkaline phosphatase (Gibco BRL) diluted 1:1000 in PBS added to each well. After a 1 h incubation at room temperature wells were washed and PNPP substrate (Pierce) added. Plates were incubated at 37° C. and absorbance at 405 nm was measured using a Titertek Multiscan MCC/340 ELISA plate reader. $T_2G_4T_2$-biotin binds to immobilized gp120 with a $K_d$ of less than 1 μM. $T_2A_4T_2$-biotin had a $K_d$ of approximately 260 μM.

Ability of ISIS 5320 to compete with dextran sulfate for binding to gp120 was determined. Biotinylated ISIS 5320 at a concentration of 0.5 μM was added to plates containing immobilized gp120 along with dextran sulfate at the indicated concentrations (Sigma, M. W. 5000). Following a 1 h incubation, the amount of oligonucleotide associated with gp120 was determined as described above. The $IC_{50}$ is between 10 and 50 μg/mL of dextran sulfate.

The site of ISIS 5320 binding to gp120 was determined by competition for binding of antisera specific for various regions of the protein. Rusche, J. R., et al., (1987) *Proc. Natl. Acad. Sci. USA* 84, 6924–6928; Matsushita, S., et al., (1988) *J. Virol.* 62, 2107–2114; Meuller, W. T., et al., (1986) *Science* 234, 1392–1395. gp120-coated microtiter plates were incubated with oligonucleotide at a concentration of 25 μM for 1 h at room temperature. Antisera was added at a dilution of 1:250 and the plates incubated 40 min. The plates were washed four times with PBS and amount of antibody bound quantitated by incubating with protein A/G-alkaline phosphatase (1:5000, Pierce) in PBS for 1 h at room temperature. After one wash with PBS, substrate was added and absorbance at 405 nm was measured.

Binding of ISIS 5320 to gp120, CD44 and CD4 expressed on cells was quantitated. HeLa cells harboring an HIV-1 env c gene; Gama Sosa, M. A., et al., (1989) *Biochem. Biophys. Res. Comm.* 161, 305–311 and Ruprecht, R. M., et al., (1991) *J. Acquir. Immune Defic. Syndr.* 4, 48–55; were cultured in DMEM supplemented with 10% FCS and 100 μg $L^{-1}$ G-418. Extent of binding to gp120 was detected using 1 μg of FITC-conjugated murine anti-gp120 HIV-1 IIIB mAb IgG (Agmed). CD44 binding was detected using 1 μg of FITC-conjugated murine anti-CD44mAb IgG (Becton-Dickinson). Each experiment consisted of 200,000 cells. Cells were washed once in culture media with 0.05% $NaN_3$ then resuspended in 100 μL of media containing oligonucleotide and incubated 15 min at room temperature. Antibody was added and the incubation continued for 1 h at 4° C. The cells were washed twice with PBS and immunofluorescence was measured on a Becton-Dickinson FACScan. Mean fluorescence intensity was determined using Lysis$^{II}$ software.

Figure 6:
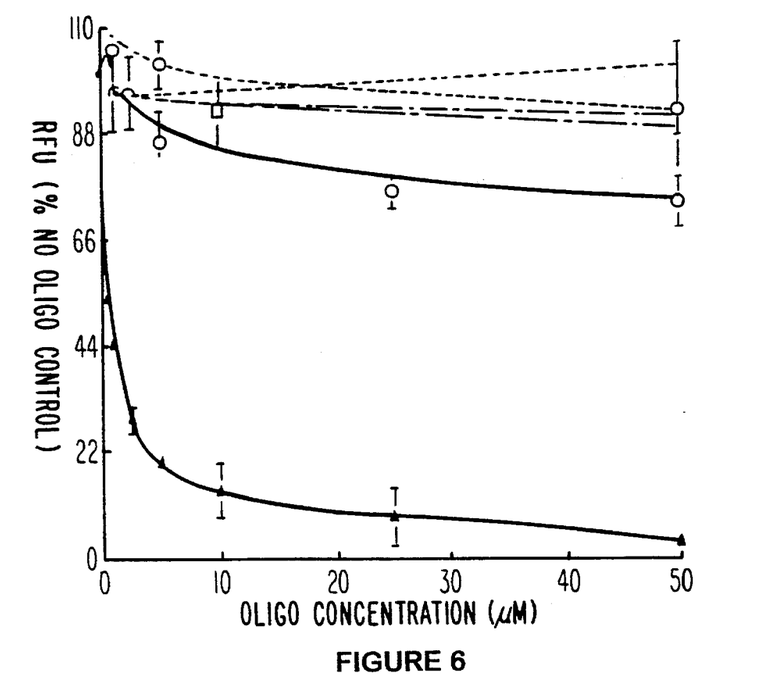
FIG. 6 is a line graph showing that ISIS 5320 blocks binding of an antibody specific for the V3 loop of gp120 (solid line) but not antibodies specific for CD44 (even dashes) or CD4 (uneven dashes), as determined by immunofluorescent flow cytometry.

CEM-T4 cells; Foley, G. E., et al., (1965) *Cancer* 18, 522–529; were maintained in MEM supplemented with 10% FCS. Extent of binding to CD4 was determined using 1 μg of Q425, a murine anti-CD4 mAb IgG. Healey, D., et al., (1990) *J. Exp. Med.* 172, 1233–1242. Cells were harvested and washed and incubated with oligonucleotide as above. After a 30 min incubation at room temperature with antibody, the cells were washed and incubated with 100 μL of media containing 5 μg of goat F $(ab')_2$ anti-mouse IgG (Pierce). The cells were incubated 30 min, washed and associated fluorescence determined as above. Results shown in FIG. 6 show that ISIS 5320 blocks binding of an antibody specific for the V3 loop of gp120 (solid line), but not antibodies specific for CD44 (even dashes) or CD4 (uneven dashes). The percent relative fluorescence units (RFU) vs. increasing concentration of ISIS 5320 (filled triangle) and scrambled control (circles) is also shown in FIG. 6.

Example 6

Selection and characterization of $T_2G_4T_2$.

A phosphorothioate oligonucleotide library containing all possible sequences of eight nucleotides divided into 16 sets, each consisting of 4,096 sequences, was prepared as described in Example 1 and screened for inhibition of HIV infection as described in Example 2. Results are summarized in Table 1.

TABLE 1

| Combinatorial Pools | X = A | X = G | X = C | X = T |
|---|---|---|---|---|
| Round 1 | | | | |
| NNA NXN NN | inactive | inactive | inactive | inactive |
| NNG NXN NN | inactive | 19.5 (5%) | inactive | inactive |
| NNC NXN NN | inactive | inactive (0%) | inactive | inactive |
| NNT NXN NN | inactive | inactive | inactive (0%) | inactive |
| Round 2 | | | | |
| NNG XGN NN | 60.7 | 1.8 (36%) | 55.6 | 56.2(3%*) |
| Round 3 | | | | |
| NNG GGX NN | 8.0 | 0.5 (94%) | 3.1(19%*) | 8.6 |
| Round 4 | | | | |
| NAG GGG XN | 0.5 | 0.5 | 0.5 | 0.5(87%) |
| NGG GGG XN | 0.5 | 0.6(99%*) | 0.4 | 0.5 |
| NCG GGG XN | 0.7 | 0.6 | 0.5 (91%) | 0.4 |
| NTG GGG XN | 0.4(82%) | 0.5 | 0.4 | 0.5 |
| Round 5 | | | | |
| XTG GGG TN | 0.2(94%) | 0.6(89%*) | 0.3 (94%) | 0.3(94%) |
| Round 6 | | | | |
| TTG GGG TX | 0.6(90%) | 0.6 | 0.5 | 0.3(93%) |

Random positions, N, are an equimolar mixture of each base. Antiviral data are reported as the quantity of drug (in μM of oligonucleotide strand) required to inhibit 50% of virus-induced cell killing ($IC_{50}$). Error in the $IC_{50}$ is ±0.1 μM. "Inactive" pools showed no antiviral activity at 100 μM strand concentration. The % tetramer, determined as described in Example 3, is given in parentheses for selected pools. An asterisk indicates multiple aggregate species.

The in vitro assay measured protection of cells from HIV-induced cytopathic effects. White, E. L., et al., (1991) *Antiviral Res.* 16,257–266. In the initial rounds of selection, antiviral activity was observed only in the set containing guanosine in two fixed positions. Subsequent rounds of selection showed that four consecutive Gs provided maximum antiviral activity. No strong selection preference was observed for nucleotides flanking the guanosine core. The sequence $T_2G_4T_2$ (oligonucleotide ISIS 5320) was chosen for further study. The concentration of ISIS 5320 required for 50% inhibition of virus-induced cell killing ($IC_{50}$) was 0.3 μM. The antiviral activity of this oligonucleotide was not a result of inhibition of cell metabolism; cytotoxic effects were not observed until cells were incubated with approximately 100 μM ISIS 5320.

Although the oligonucleotide ISIS 5320 has a phosphorothioate backbone, evidence suggests that it adopts a four-stranded, parallel helix as do phosphodiester oligonucleotides of similar sequence. Cheong, C. & Moore, P. B. (1992) *Biochemistry* 31, 8406–8414; Aboul-ela, F., et al., (1992) *Nature* 360, 280–282; Sarma, M. H., et al., (1992) *J. Biomol. Str. Dyn.* 9, 1131–1153; and Wang, Y. & Patel, D. J. (1992) *Biochemistry* 31, 8112–8119. The oligonucleotides in the combinatorial library pools that show antiviral activity (Table 1) and oligonucleotide ISIS 5320 form multimeric complexes as shown by size exclusion chromatography (FIG. 1). The retention time of the complex was that expected for a tetrameric species based on plots of retention time vs. log molecular weight of phosphorothioate oligonucleotide standards (data not shown). The circular dichroism (CD) spectrum of the multimeric form of oligonucleotide ISIS 5320 is characterized by a peak at 265 nm and a trough at 242 nm (data not shown), similar to the spectra reported by others for deoxyoligonucleotide tetramers. Sarma, M. H., et al., (1992) *J. Biomol. Str. Dyn.* 9, 1131–1153; Lu, M., Guo, Q. & Kallenbach, N. R. (1992) *Biochemistry* 31, 2455–2459; Jin, R., et al., (1992) *Proc. Natl. Acad. Sci. USA* 89, 8832–8836 and Hardin, C. C., et al., (1992) *Biochemistry* 31, 833–841. It has been reported that when two phosphodiester oligonucleotides of dissimilar size, but each containing four or five guanosines in a row, are incubated together, five distinct aggregate species are formed on a non-denaturing gel Sen, D. & Gilbert, W. (1990) *Nature* 344, 410–414 and Kim, J., Cheong, C. & Moore, P. B. (1991) *Nature* 351, 331–332. In principle, only a tetramer of parallel strands can explain this pattern. When this experiment was performed with two phosphorothioate oligonucleotides, the antiviral oligonucleotide ISIS 5320 and a 21-residue oligonucleotide containing 4 guanosines near the 3' end ($^5T_{13}G_4T_4^{3'}$; SEQ ID NO: 4), the five aggregate species expected for a parallel-stranded tetramer were observed on a non-denaturing gel (FIG. 2). Example 7

The tetramer is active against HIV.

Oligonucleotides were screened for antiviral activity as described in Example 4. Samples of ISIS 5320 were diluted from a 1 mM stock solution that was at least 98% tetramer. Results showed that the tetramer is stable indefinitely at 1 mM strand concentration; no decrease in tetramer was observed over 5 months in a 1 mM sample in buffer containing 100 mM KCl at room temperature. Upon dilution to concentrations used in antiviral assays (less than 25 µM) dissociation of the tetramer begins; however, kinetics of the dissociation are very slow (FIG. 3). Slow kinetics for association and dissociation of intermolecular G-quartet complexes have been reported. Jin, R., et al., (1992) *Proc. Natl. Acad. Sci. USA* 89, 8832–8836 and Sen, D. & Gilbert, W. (1990) *Nature* 344, 410–414. The half life for the dissociation of the potassium form of ISIS 5320 is about 45 days. During the six-day period of the acute antiviral assay, at least 70% of the sample remained in the tetramer form whether the sample was prepared in sodium or potassium. Both sodium and potassium forms have the same $IC_{50}$ values in the acute antiviral assay, even though potassium preferentially stabilized the tetramer.

Heat denaturation of the tetrameric complex formed by ISIS 5320 before addition to the antiviral assay resulted in loss of activity; antiviral activity was recovered upon renaturation (data not shown). The striking difference in antiviral activity among the initial 16 sets of oligonucleotides used for combinatorial screening can be explained by the presence or absence of the G-core and therefore the tetramer structure (Table 1). In the initial round of screening, approximately 12% of the molecules in the active $^5$NNGNGNNN$^{3'}$ pool contained at least four sequential Gs, and size exclusion chromatography showed that 5% of the oligonucleotides formed tetramers (Table 1). In contrast, in the other three round 1 pools where X=G only 0.4% of the molecules contained at least four sequential Gs and no tetramer was observed. In other pools, there were no molecules with four consecutive Gs.

Deletion of nucleotides from either end of the ISIS 5320 sequence resulted in a loss of activity (Table 2).

TABLE 2

| Sequence | $IC_{50}$ (µM) | % tetramer |
|---|---|---|
| $T_sT_sG_sG_sG_sG_sT_sT$ | 0.3 | 98 |
| $T_sT_sG_sG_sG_sG_sT_sT$ heat denatured | inactive | 0 |
| $G_sG_sG_sG_sT_sT$ | 0.5 | 94* |
| $G_sG_sG_sG_sT$ | 1.4 | 61* |
| $G_sG_sG_sG$ | 4 | 29* |
| $T_sT_sG_sG_sG_sG$ | 13 | 40* |
| $T_sG_sG_sG_sG$ | inactive | 57* |
| $T_sG_sT_sG_sT_sG_sT_sG$ | inactive | 0 |
| $\alpha$-$T_sT_sG_sG_sG_sG_sT_sT$ | 0.5 | 98 |
| $\alpha$-$T_oT_oG_oG_oG_oG_oT_oT$ | inactive | 97 |
| $T_oT_oG_oG_oG_oG_oT_oT$ | inactive | 93 |
| $T_sT_sG_oG_oG_oG_sT_sT$ | 5.0 | 80 |
| $T_oT_sG_sG_sG_sG_oT_oT$ | inactive | 72 |
| $T_oT_sG_oG_sG_oG_sT_oT$ | inactive | 90 |
| $T_sT_sG_oG_oG_oG_sT_sT$ | 5.3 | 83 |
| $T_sT_sG_sG_sG_sG_sT_sT_sB$ | 0.4 | 85 |

Data from the acute HIV assay for sequence variants and analogs of ISIS 5320. Chemical modifications of the oligonucleotide are indicated: "s" phosphorothioate backbone, "o" phosphodiester backbone, "α", α-configuration of the glycosidic bond; "B" biotin (incorporated during chemical synthesis using biotin linked CPG from Glen Research). "Inactive" indicates no activity at 25 µM concentration. The % tetramer was determined as described for FIG. 1. An asterisk indicates more than one aggregate species.

The phosphorothioate GGGG shows some activity; two nucleotides on the 3' side of the four Gs were required for nearly optimal activity. More than one multimeric species was observed by size exclusion chromatography for oligonucleotides with the G-core exposed.

The sequence $T_2G_4T_2$ with a phosphodiester backbone was inactive in the anti-HIV assay, even though the phosphodiester tetramer appears to be kinetically more stable than that formed by the phosphorothioate ISIS 5320 (FIG. 3). While not wishing to be bound to a particular theory, two hypotheses are proposed. The phosphorothioate backbone may be mechanistically required or the modified backbone may prevent nuclease-mediated degradation of the oligonucleotide.

Oligonucleotide analogs with the glycosidic bond oriented in the α-position (alpha anomeric configuration) are resistant to nuclease degradation. Morvan, F., et al., (1993) *Nucleic Acids Res.* 15, 3421–3437. Based on size exclusion chromatography it has been shown that both the phosphorothioate α-oligonucleotide and the phosphodiester α-oligonucleotide formed tetramers however, only the phosphorothioate analog was active against HIV (Table 2). Assay of oligonucleotides with mixed phosphorothioate-phosphodiester backbones showed that phosphorothioate linkages at the termini, but not within the G-core, are necessary for activity. Results are shown in Table 2.

Example 8

Tetramer inhibits viral binding or fusion to CD4$^+$ cells.

The oligonucleotide ISIS 5320 had no effect on chronically infected (H9 IIIB) cell models (data not shown) that respond only to inhibitors that work at post-integration steps. In a high multiplicity of infection (MOI) experiment performed as described in Srivastava, K. K., et al., (1991) *J. Virol.* 65, 3900–3902, ISIS 5320 inhibited production of intracellular PCR-amplifiable DNA (data not shown), which indicated that the compound inhibited an early step of HIV replication, such as binding, fusion, internalization, or reverse transcription.

The tetramer form of ISIS 5320 also inhibited binding or fusion of infectious virus to a CD4+ cell. The assay was performed as described in Example 4. HeLa-CD4-LTR-B-gal cells; Kimpton, J. & Emerman, M. (1992) *J. Virol.* 66, 2232–2239; were incubated for 15 minutes with oligonucleotide at 37° C. prior to the addition of virus. After 1 hour, the cells were washed to remove unbound virus and oligonucleotide. During the incubation period, virus binding and membrane fusion events occur. Srivastava, K. K., et al., (1991) *J. Virol.* 65, 3900–3902. Extent of infection after 48 hours was determined by quantitation of syncytia and ELISA as previously described in Kimpton, J. & Emerman, M. (1992) *J. Virol.* 66, 2232–2239. At a ISIS 5320 concentration of approximately 0.4 µM, virus production was reduced to 50% of control (data not shown). Heat-denatured ISIS 5320 and $^5$'TGTGTGTG$^3$' showed inhibition of binding at 5 µM oligonucleotide concentration. These fusion and binding inhibition experiments strongly suggest that the tetramer form of ISIS 5320 inhibits viral infection at a very early step, either during binding of the virion to the cell or during the early events of fusion and internalization of the virion.

Example 9

Tetramer binds to the V3 domain of gp120.

Figure 4:
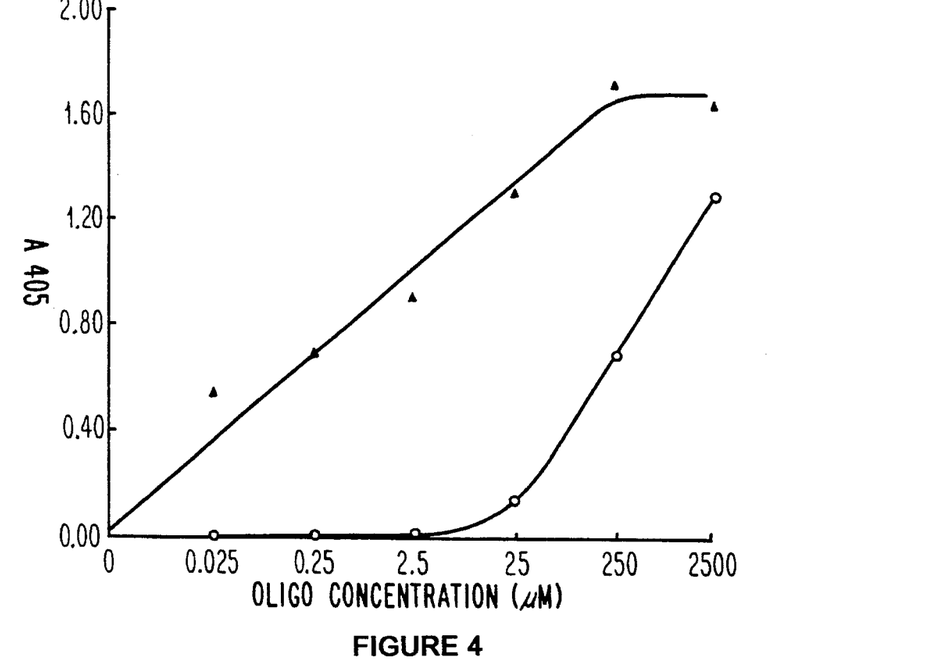
FIG. 4 is a line graph showing binding of ISIS 5320 to gp120, measured by absorbance at 405 nm.

Cellular experiments indicated that ISIS 5320 blocks viral binding or fusion, therefore, the affinities of the ISIS 5320 tetramer for CD4 and gp120 were determined as described in Example 5. Biotinylated ISIS 5320 (Table 2) bound to immobilized gp120 with a dissociation constant ($K_d$) of less than 1 µM (FIG. 4). In contrast, a control phosphorothioate, $^5$'T$_2$A$_4$T$_2$-biotin$^3$' bound weakly to gp120 with an estimated $K_d$ of 260 µM. Addition of CD4 at concentrations of up to 50 µg mL$^{-1}$ had no effect on ISIS 5320 binding to gp120 (data not shown). Similar experiments using CD4-coated microtiter plates showed that biotinylated ISIS 5320 also associates with CD4; however, the $K_d$ of approximately 25 µM was considerably weaker than to gp120. The control bound CD4 only when it was added at very high concentrations ($K_d$ approximately 240 µM). In addition, qualitative gel shift assays performed as described in Fried, M. & Crothers, D. M. (1981) *Nucleic Acids Res.* 9, 6505–6525, were performed to determine the affinity of ISIS 5320 for other HIV proteins (Tat, p24, reverse transcriptase, vif, protease, gp41), soluble CD4 (sCD4) and non-related proteins (BSA, transferrin and RNase V$_1$). Both monomeric and tetrameric forms of ISIS 5320 bound to BSA and reverse transcriptase. Tetramer-specific binding was observed only to gp120 and sCD4.

Figure 5:
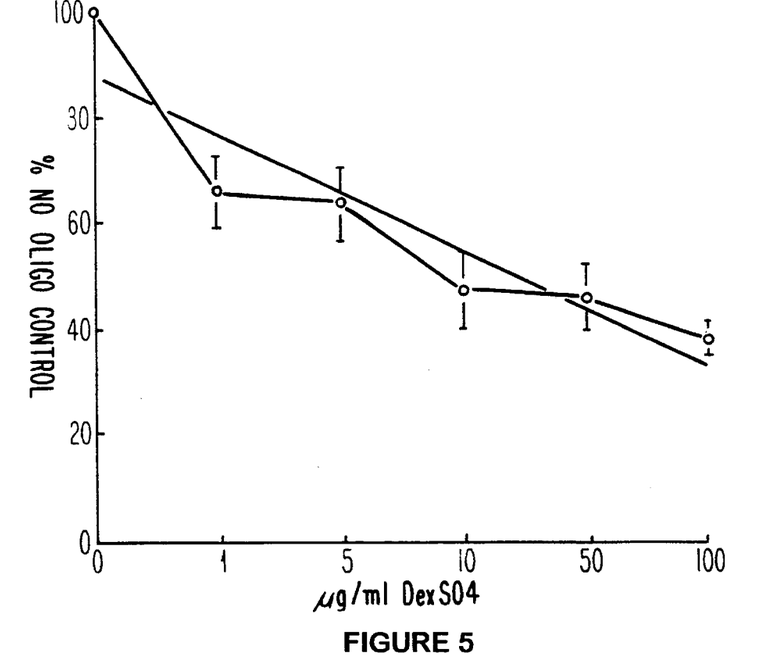
FIG. 5 is a line graph showing that dextran sulfate is a competitive inhibitor of binding of biotinylated ISIS 5320 to gp120.

The V3 loop of gp120 (amino acids 303–338) is considered the principal neutralizing domain of the protein; peptides derived from this region elicit type-specific neutralizing antibodies that block viral infection by blocking fusion. (1992) *Human Retroviruses and AIDS* 1992, eds. Myers, G. et al. (Theoretical Biology and Biophysics, Los Alamos National Laboratory, Los Alamos, N. Mex.). The V3 loop of gp120 is also the site of action of anionic polysaccharides, such as dextran sulfate, that inhibit viral binding, replication and syncytium formation. Callahan, L., et al., (1991) *J. Virol.* 65, 1543–1550. Dextran sulfate is a competitive inhibitor of binding of biotinylated ISIS 5320 to gp120 immobilized on a microtiter plate. About 50% of the tetramer binding was inhibited at a dextran sulfate concentration between 10 and 50 µg mL$^{-1}$ (FIG. 5). Dextran sulfate has been shown to inhibit binding of gp120-specific antibodies to gp120 in this concentration range. Callahan, L., et al., (1991) *J. Virol.* 65, 1543–1550.

The oligonucleotide ISIS 5320 also interferes with binding of antisera directed against the V3 loop region of gp120, but not to antisera specific for another region of the protein. Rusche, J. R., et al., (1987) *Proc. Natl. Acad. Sci. USA* 84, 6924–6928; Matsushita, S., et al., (1988) *J. Virol.* 62, 2107–2114 and Meuller, W. T., et al., (1986) *Science* 234, 1392–1395. The control oligonucleotide had no effect on antibody binding.

The tetramer also binds to the V3 loop of gp120 expressed on cells. Binding of a monoclonal antibody specific the V3 loop of gp120 was inhibited by ISIS 5320 at a concentration of approximately 0.5 µM ($K_i$) determined using immunofluorescent flow cytometry (FIG. 6). The control oligonucleotide had little effect on binding at concentrations up to 50 µM. Neither oligonucleotide significantly decreased binding of antibodies directed to human CD44 on the same cells or to CD4; Healey, D., et al., (1990) *J. Exp. Med.* 172, 1233–1242. on CEM-T4 cells.

Phosphorothioate oligonucleotides of at least 15 nucleotides are known to be non-sequence-specific inhibitors of HIV. Stein, C. A., et al., (1991) *J. Acquit. Immune Defic. Syndr.* 4, 686–693. In the acute assay system used here, previously tested phosphorothioate oligonucleotides of 18 to 28 nucleotides in length have IC$_{50}$ values between 0.2 and 4 µM. Vickers, T., et al.,(1991) *Nucleic Acids Res.* 19, 3359–3368. Stein and co-workers have shown that phosphorothioate oligonucleotides of at least 18 nucleotides in length, bind to the V3 loop of gp120 (40), and to the CD4 receptor and other cell surface antigens. Stein, C. A., et al.,(1991) *J. Acquir. Immune Defic. Syndr.* 4, 686–693. Variation in the binding and antiviral activities of long mixed sequence oligonucleotides likely result from folding into unknown structures with varying affinities for membrane surface proteins. In contrast, ISIS 5320 adopts a defined tetrameric structure. The antiviral activity is 2- to 25-fold better, on a weight basis, than that of longer linear oligonucleotides.

ELISA assays were performed to determine whether ISIS 5320 was capable of blocking the interaction between CD4 and gp120 (data not shown). Addition of increasing amounts of ISIS 5320 decreased binding of CD4 to immobilized gp120; 50% of binding was inhibited at a concentration of approximately 2.5 µM. The control oligonucleotide ($^5$'TGTGTGTG$^3$') had no effect on the CD4/gp120 interaction. These results were confirmed in a gp120-capture ELISA assay in which the microtiter plates were coated with CD4 (IC$_{50}$ approximately 20 µM). Compounds that bind to the V3 loop of gp120 can inhibit fusion without completely blocking the interaction between CD4 and gp120. Callahan, L., et al., (1991) *J. Virol.* 65, 1543–1550. Unlike ISIS 5320, dextran sulfate does not prevent the gp120/CD4 interaction in an ELISA assay even at concentrations 10,000-fold above its IC$_{50}$ Callahan, L., et al., (1991) *J. Virol.* 65, 1543–1550.

The tetrameric form of phosphorothioate T$_2$G$_4$T$_2$ blocks cell-to-cell and virion-to-cell spread of HIV infection by binding to the gp120 V3 loop. The tetramer provides a rigid, compact structure with a high thio-anionic charge density that may be the basis for its strong interaction with the cationic V3 loop. Although the V3 loop is a hypervariable region, the functional requirement for cationic residues in the V3 loop may limit the virus's capability to become resistant to dense polyanionic inhibitors. Compounds derived from the G-quartet structural motif are potential candidates for use in anti-HIV chemotherapy.

What is claimed is:

1. An oligonucleotide TTGGGGTT wherein at least one linkage is a phosphorothioate.

* * * * *

UNITED STATES PATENT AND TRADEMARK OFFICE
CERTIFICATE OF CORRECTION

PATENT NO. : 5,523,389
DATED : June 4, 1996
INVENTOR(S) : David J. ECKER et al.

It is certified that error appears in the above-indentified patent and that said Letters Patent is hereby corrected as shown below:

In Other Publications, column 2, at line 3 of Ecker et al. reference, delete "l" before the number "21";

At column 7, lines 13 and 14, delete "Motvan" and insert --Morvan--;

At column 7, line 14, delete "Raynet" and insert --Rayner--;

At column 9, line 32, delete "$L^{-1}$" and insert --$\mu L^{-1}$--;

At column 11, line 27, insert a return before the word "Example".

Signed and Sealed this

Twenty-fourth Day of September, 1996

Attest:

BRUCE LEHMAN

Attesting Officer      Commissioner of Patents and Trademarks